United States Patent [19]
Liberti et al.

[11] Patent Number: 5,876,593
[45] Date of Patent: Mar. 2, 1999

[54] MAGNETIC IMMOBILIZATION AND MANIPULATION OF BIOLOGICAL ENTITIES

[75] Inventors: Paul A. Liberti, Huntingdon Valley; Yuzhou Wang, Wayne, both of Pa.

[73] Assignee: Immunivest Corporation, Wilmington, Del.

[21] Appl. No.: 931,067

[22] PCT Filed: Sep. 15, 1997

[86] PCT No.: PCT/US93/11087

§ 371 Date: Apr. 24, 1995

§ 102(e) Date: Apr. 24, 1995

[87] PCT Pub. No.: WO94/11078

PCT Pub. Date: May 26, 1994

Related U.S. Application Data

[63] Continuation of Ser. No. 424,271, filed as PCT/US93/11087 Nov. 16, 1993 published as WO94/11078 May 26, 1994, abandoned, which is a continuation of Ser. No. 976,476, Nov. 16, 1992, abandoned, which is a continuation of Ser. No. 588,662, Sep. 26, 1990, Pat. No. 5,200,084.

[51] Int. Cl.[6] .................................................. B01D 35/06
[52] U.S. Cl. .............................................. 210/95; 210/222
[58] Field of Search ............................... 210/94, 95, 222, 210/223, 695; 356/246; 209/223.1, 232, 217; 436/526

[56] References Cited

U.S. PATENT DOCUMENTS

| | | |
|---|---|---|
| 3,567,026 | 3/1971 | Kolm . |
| 3,676,337 | 7/1972 | Kolm . |
| 3,902,994 | 9/1975 | Maxwell et al. . |
| 3,970,518 | 7/1976 | Giaever . |
| 4,018,886 | 4/1977 | Giaever . |

(List continued on next page.)

FOREIGN PATENT DOCUMENTS

| | | |
|---|---|---|
| 0030087 | 6/1981 | European Pat. Off. . |
| 0149565 | 7/1985 | European Pat. Off. . |
| 60-177265 | 9/1985 | Japan . |
| 2044635 | 10/1980 | United Kingdom .................. 210/222 |
| 1578396 | 11/1980 | United Kingdom . |
| WO8706345 | 10/1987 | WIPO . |

OTHER PUBLICATIONS

Immunoassays for Clinical Chemistry, pp. 147–162 Hunter et al. eds.

The properties of magnetic supports in Relation to Immobilized Enzyme Reactors Robinson et al. Biotechnology amd Bioengineering vol. XV (1973).

(List continued on next page.)

*Primary Examiner*—Matthew O. Savage
*Attorney, Agent, or Firm*—Dann Dorfman Herrell & Skillman, P.C.

[57] ABSTRACT

Biological entities such as cells, microbes, or components thereof are labeled with a magnetic colloid containing microscopic magnetic particles. The magnetic particles have a coating capable of biospecific or non-specific binding with the entities. An immobilization apparatus includes a non-magnetic vessel having a ferromagnetic collection structure for attracting the entities toward a collection surface upon which the magnetically labeled entities are immobilized subsequent to placement of the vessel on a support between two magnets. The ferromagnetic collection structure preferably has a sharp edge or high curvature for intensifying the magnetic field and for collecting the entities in a monolayer. The vessel includes an un-obstructed observation path so that immobilized entities may be observed and/or manipulated. The ferromagnetic collection structure may be arranged in various two dimensional patterns to provide a desired collection configuration. The apparatus may further have inlet and outlet ports for allowing a flow of liquid reagent through the vessel for washing or straining the immobilized entities. The support can be translated so that a shoulder on the collection structure concentrates the collected entities by movement of the shoulder in a transverse direction relative to the magnetic field.

11 Claims, 4 Drawing Sheets

U.S. PATENT DOCUMENTS

| | | |
|---|---|---|
| 4,141,687 | 2/1979 | Forrest et al. . |
| 4,230,685 | 10/1980 | Senyei et al. . |
| 4,267,234 | 5/1981 | Rembaum . |
| 4,375,407 | 3/1983 | Kronick . |
| 4,452,773 | 6/1984 | Molday . |
| 4,526,681 | 7/1985 | Friedlaender et al. . |
| 4,554,088 | 11/1985 | Whitehead et al. . |
| 4,576,927 | 3/1986 | Kuroda et al. . |
| 4,659,678 | 4/1987 | Forrest et al. . |
| 4,663,029 | 5/1987 | Kelland et al. . |
| 4,737,294 | 4/1988 | Kukuck . |
| 4,772,383 | 9/1988 | Christensen . |
| 4,784,767 | 11/1988 | Hasada et al. . |
| 4,795,698 | 1/1989 | Owen et al. . |
| 4,855,045 | 8/1989 | Reed et al. . |
| 4,895,650 | 1/1990 | Wang . |
| 4,910,148 | 3/1990 | Sorenson . |
| 4,988,618 | 1/1991 | Li et al. . |
| 5,055,190 | 10/1991 | Hayes et al. . |
| 5,200,084 | 4/1993 | Liberti et al. . |

OTHER PUBLICATIONS

The Dynal MPC–1 (manufacturing by DYNAL Inc., Great Neck, NY) product information sheet (1987).

BioMag Separator (manufactured by Advanced Magnetics, Inc., Cambridge, ma catalog pp. (4 sheets).

Magnetic Separator (manufactured by Ciba–Corning Medical Diagnostics, Wampole, MA catalog cover and catalog pages (2 sheets).

Magnetic Separator (Made by Miltenyi Biotech GmbH, Gladbach, Germany product information literature.

High Gradient Magnetic Separation Theory and Applications, R.R. Oder, IEEE Transactions on Magnetics, vol. MAG–12, No. 5, Sep. 1976.

Magnetic Separator (made by Serono Diagnostics, Norwell, MA catalog pp. (1 sheet).

Magnetite–Protein Conjugates for the Separation of Cells by High Gradient Magnetic Filtration, C.S. Owen et al., Cell Separation Methods and Selected Applications, vol. 4, 1987.

Magnetic Separation Techniques: Their Application to Medicine, J. T. Kemshead et al., Molecular and Cellular Biochemistry, 67:11–18 (1985).

Magnetic Solid–Phase Radioimmunoassay, L.S. Hersh et al., Clinica Chimica Acta 63:69–72 (1975).

High Gradient Magnetic Separation II. Single Wire Studies of Shale Oils Takayasu et al., IEEE Transactions on Magnetics, vol. MAG–18, No. 6 (1982).

A Bench Top Magnetic Separator for Malarial Parasite Concentration Paul et al., IEEE Transactions on Magnetics, vol. MAG–17, No. 6, (1981).

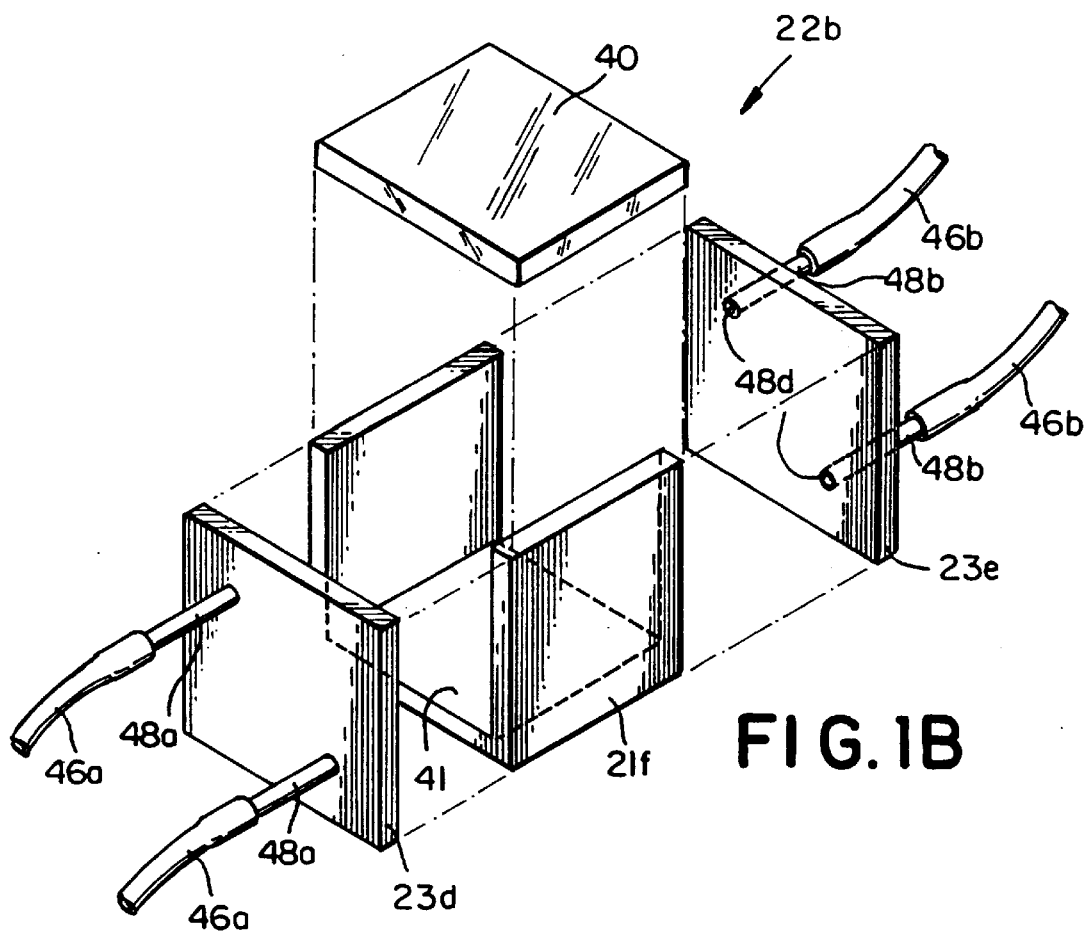
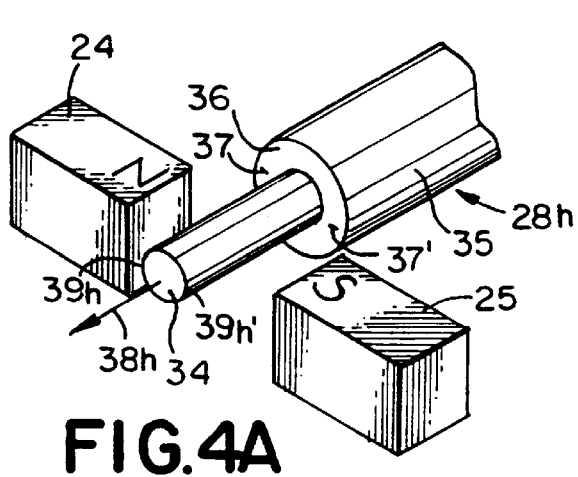
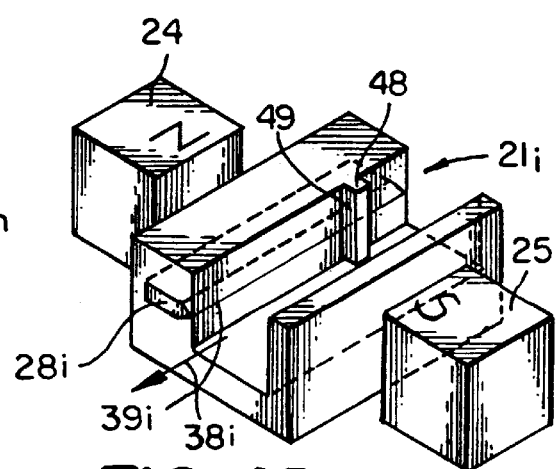

MAGNETIC IMMOBILIZATION AND MANIPULATION OF BIOLOGICAL ENTITIES

This application is a continuation of U.S. patent application Ser. No. 08/424,271, filed Apr. 24, 1995, now abandoned, which was a U.S. national stage application of PCT/US93/11087, filed Nov. 16, 1993, which was a continuation of U.S. patent application Ser. No. 07/976,476, filed Nov. 16, 1992, now abandoned, which was a continuation of U.S. patent application Ser. No. 07/588,662, filed Sep. 26, 1990, now U.S. Pat. No. 5,200,084.

FIELD OF THE INVENTION

This invention relates to the immobilization and manipulation of microscopic biological entities. More particularly, the present invention relates to magnetic labelling and immobilization of microscopic biological entities within an apparatus having an observation path for allowing observation and manipulation of such entities suspended within a fluid medium.

BACKGROUND

Many biological techniques such as are employed in biotechnology, microbiology, clinical diagnostics and treatment, in vitro fertilization, hematology and pathology, require such processes as identification, separation, culturing, or manipulation of a target entity such as a type of cell or microbe within a fluid medium such as blood, other bodily fluids, culture fluids or samples from the environment. It is often desirable to retain viability of the target entity or to culture the target entity.

Identification techniques typically involve labelling the target entity with a reagent which can be detected according to a characteristic property. Entities which can be viewed optically such as cells or certain microbes, may be identified using fluorescent MAb's or staining reagents specific to certain classes of cells or microbes. When such identification is done manually or mechanically, as by microscopy, multiple operations involving incubations and washing steps to remove excess labelling reagent are often performed. For example, in the usual method used to identify a subset of T-lymphocytes, such as T-Helper Cells or CD4-positive cells, a mixture of peripheral blood lymphocytes is incubated with a fluorescent MAb directed to CD4-positive cells. The MAb is then given sufficient incubation time to react with the CD4-positive cells. The CD4-positive cells are then washed using multiple centrifugations and can then readily be identified by fluorescent microscopy.

In the practice of manual fluorescent labelling methods employing a fluorescent microscope, direct labeling with MAb's is often impractical due to the expense of obtaining a cell-specific fluorescent Mab and because of reduced signal availability. Thus the technique of indirect analysis is common. During indirect analysis, the target entities are first labeled with a specific non-fluorescent MAb. Excess Mab is washed away. Then, a fluorescent-labeled second reagent such as fluorescent-labeled goat anti-mouse antibody is added to the medium. The medium is allowed to incubate to allow the labelled second reagent to bind with the non-fluorescent MAb and then excess reagent is removed. The target entities may then be identified due to the attachment of the fluorescent secondary reagent to the non-fluorescent biospecific MAb. Such methods are time-consuming, costly, and require considerable quantities of reagents. Moreover, as the number of operations employed in such identification processes increases, a greater number of target entities are lost or killed. Accurate microbial analyses employing such methodologies are difficult to achieve because of the small numbers of target entities involved as well as the difficulty of washing away unbound labeling agents. Other methodologies such as flow cytometry (fluorescent activated cell sorting) or field flow fractionation can be used for such analysis and in some instances require fewer manipulations. These other methods, however, require expensive equipment, highly trained personnel and typically can only analyze or separate one sample at a time.

Manipulation of target entities required by other biological techniques may also involve such processes as insertion of genetic material, organelles, subcellular components, viruses, or other foreign materials or bodies into the target entities. Inserted materials can be labeled prior to insertion so that effects and movements of these materials can be studied during incubation of the medium. In techniques such as transfection, or in vitro fertilization mechanical probes or arms are often used to hold the target entities. Such mechanical holding methods tend to obscure or damage the target entities.

It would be desirable in such biotechnical procedures as have been discussed to provide devices and methods for precise non-destructive immobilization and manipulation of specific target entities in an inexpensive and rapid manner.

Magnetic colloids having particles coated with biospecific compounds which attach to target entities are known to be useful in certain biospecific separation techniques. Reaction rates between such colloidal particles and target entities can be relatively rapid due to fast kinetic activity of the particles and sufficiently large areas of exposed reactant coatings. Magnetic particles in the range of 0.7 to 1.5 microns have been described in U.S. Pat. Nos. 3,790,518; 4,018,886; 4,230,685; 4,267,234; 4,452,773; 4,554,088; and 4,659,678. Certain of these particles are disclosed to be useful solid supports for immunologic reagents, having reasonably good suspension characteristics when mildly agitated. Magnetic particle suspensions presently in commercial use tend to flocculate in time and must be resuspended by agitation prior to use. Such agitation adds another step to any process employing such reagents.

Small magnetic particles, such as those mentioned above, generally fall into two broad categories: particles that are permanently magnetized; and particles that become magnetic when subjected to a magnetic field. The latter particles are referred to herein as magnetically-responsive particles. Materials displaying magnetically-responsive behavior are sometimes described as superparamagnetic. However, certain ferromagnetic materials such as magnetic iron oxide crystals, behave in a magnetically-responsive manner when the crystals are less than about 30 nm in diameter. Larger crystals of ferromagnetic materials, by contrast, retain permanent magnet characteristics after exposure to a magnetic field and tend to aggregate thereafter. The properties of such particles are described in P. Robinson et al., Biotech Bioeng. XV:603-06 (1973).

Magnetically-responsive colloidal magnetite is disclosed in U.S. Pat. No. 4,795,698 to Owen et al., which relates to polymer-coated, sub-micron size magnetite particles that behave as true colloids. Several devices are known which are used to separate magnetic particles from colloidal suspensions. Examples of such devices are magnetic separators such as the MAIA Magnetic Separator manufactured by Serono Diagnostics, Norwell, Mass.; the DYNAL MPC-1 manufactured by DYNAL, Inc., Great Neck, N.Y.; and the BioMag Separator, manufactured by Advanced Magnetics, Inc., Cambridge, Mass. A similar magnetic separator, manufactured by Ciba-Corning Medical Diagnostics, Wampole, Mass. is provided with rows of bar magnets arranged in parallel and located at the base of the separator. This device accommodates 60 test tubes, with the closed end of each test tube fitting into a recess between two of the bar magnets.

The above-described magnetic separators have the disadvantage that the magnetic particles and other impurities tend to form several layers on the inner surface of the sample container where they become entrapped and are difficult to remove even with vigorous washing. These separators are also not capable of establishing monolayers of target entities for microscopic analysis or manipulation.

Separation of magnetically-responsive particles within colloidal suspensions requires high gradient field separation techniques such as are described in R. R. Oder, *IEEE Trans. Magnetics*, 12:428-35 (1976); C. Owen and P. Liberti, *Cell Separation: Methods and Selected Applications*, Vol. 5, Pretlow and Pretlow eds., Academic Press, NY, (1986). Gradient fields normally used to filter such materials generate relatively large magnetic forces. Another useful technique for performing magnetic separation of colloidal magnetic particles from a test medium by the addition of agglomerating agents is disclosed in and commonly-owned U.S. Pat. No. 5,108,933 issued Apr. 28, 1992.

A commercially available high gradient magnetic separator, the MACS device made by Miltenyi Biotec GmbH, Gladback, West Germany, employs a column filled with a non-rigid steel wool matrix in cooperation with a permanent magnet. In operation, the enhanced magnetic field gradient produced in the vicinity of the steel wool matrix attracts and retains the magnetic particles while the non-magnetic components of the test medium pass through the column. It has been found that the steel wool matrix of such prior art high-gradient magnetic separation (HGMS) devices often causes non-specific entrapment of biological entities other than the target entities. The entrapped non-magnetic components cannot be removed completely without extensive washing and resuspension of the particles bearing the target substance. Moreover, the sizes of the columns in many of the prior art HGMS devices require substantial volumes of test media, which poses an impediment to their use in performing various useful laboratory-scale separations. In addition, the steel wool matrix may damage sensitive cell types.

Although HGMS affords certain advantages in performing medical or biological analyses based on biospecific affinity reactions involving colloidal magnetic particles, the systems developed to date are not particularly suited for immobilization and micromanipulation. For example, collection of microscopic entities upon an irregular structure such as steel wool is not conducive to microscopic observation wherein it is desirable to maintain the subject of interest in the focal plane of a microscope. Furthermore, the convoluted surface of the steel wool would obscure observation of the collected entities. Accordingly, it would be desirable to provide an HGMS apparatus for immobilization and micromanipulation of target entities which is of relatively simple construction and operation and yet maximizes magnetic field gradients, so as to be of practical utility in conducting various laboratory-scale separations and micromanipulations.

SUMMARY OF THE INVENTION

According to one aspect of the present invention an apparatus is provided for immobilizing selected microscopic biological entities within a non-magnetic vessel containing a fluid medium. A colloidal suspension of submicroscopic magnetically-responsive particles having a biospecific coating for binding with the selected entities is introduced into the medium, the particles become attached to the selected entities, and are subsequently attracted to a collection structure within or adjacent to the interior of the vessel that produces an intense magnetic field gradient upon application of an external magnetic field by a magnet structure having poles in opposition on either side of the vessel. Alternatively, non-specific binding to some or all of the entities can be employed.

The spatial distribution in which entities are collected is related to the shape of the ferromagnetic collection structure and the concentration of magnetically-responsive particles in the fluid medium. The ferromagnetic collection structure provides a collection surface upon which the target entities are immobilized in an orderly manner so that observation and/or manipulation of the immobilized entities is easily accomplished relative to known techniques.

Ferromagnetic collection structures having sufficiently high curvatures, a multi-stranded construction, or sharp edges are capable of producing substantially monolayered one-dimensional spatial distributions of immobilized entities. Additionally, the concentration of magnetically-responsive particles may be selected to facilitate the formation of such a monolayer, for example by controlling the concentration of magnetically-responsive particles suitable to bind with target entities such that the surface area of the bound target entities is commensurate with the surface area of the ferromagnetic collection structure or other collection surface within the magnet separator.

A non-magnetic vessel for use in a magnetic immobilization apparatus of the invention preferably has an observation path which allows microscopic observation of the immobilized entities. According to one aspect of the invention, the observation path includes at least one open or transparent aperture or surface in the non-magnetic vessel for allowing substantially unobscured microscopic observation and physical manipulation, such as microsurgery, of the immobilized entities. According to another aspect of the invention, the vessel may include at least one surface or aperture that is transparent to at least a portion of the electromagnetic spectrum required for a particular observational technique. The observation path is oriented relative to the collection structure to allow substantially unobscured observation of the immobilized entities. The collection structure is preferably arranged to maintain a plurality of the immobilized entities within an orderly array intersecting the observation path, such as within a focal plane of a microscope.

A vessel may further have ports which allow a flow of liquid reagents through the vessel as may be desired in, for example, sequential reaction techniques. The flowthrough vessel also facilitates observation of the immobilized entities by allowing the test medium to be flushed or rinsed. Such flushing or rinsing may be employed to remove an opaque test medium from the vessel while leaving behind the immobilized entities or substances. Furthermore, flushing or rinsing of the test medium allows control of the duration of the separation process so that the test medium may be removed from the vessel after having been placed in the magnetic field for a period of time sufficient for formation of a monolayered array of immobilized entities upon the collection structure and within the observation path.

In accordance with another aspect of the invention, an apparatus may provide for lateral translation or concentration of immobilized entities by the use of a transverse obstruction, or shoulder, which concentrates immobilized entities in the vicinity of the obstruction, or shoulder, as the shoulder is moved laterally along the axis of the collection structure within or out of the field confined to the region between the opposing poles.

BRIEF DESCRIPTION OF THE DRAWINGS

The foregoing summary, as well as the following detailed description of a preferred embodiment of the present invention, will be better understood when read in conjunction with the appended drawings, in which:

FIGS. 1A–1C are exploded views of embodiments of a magnetic immobilization apparatus;

FIGS. 4A and 4B are overhead perspective views of devices for collecting and concentrating target entities.

DETAILED DESCRIPTION

Figure 1A:
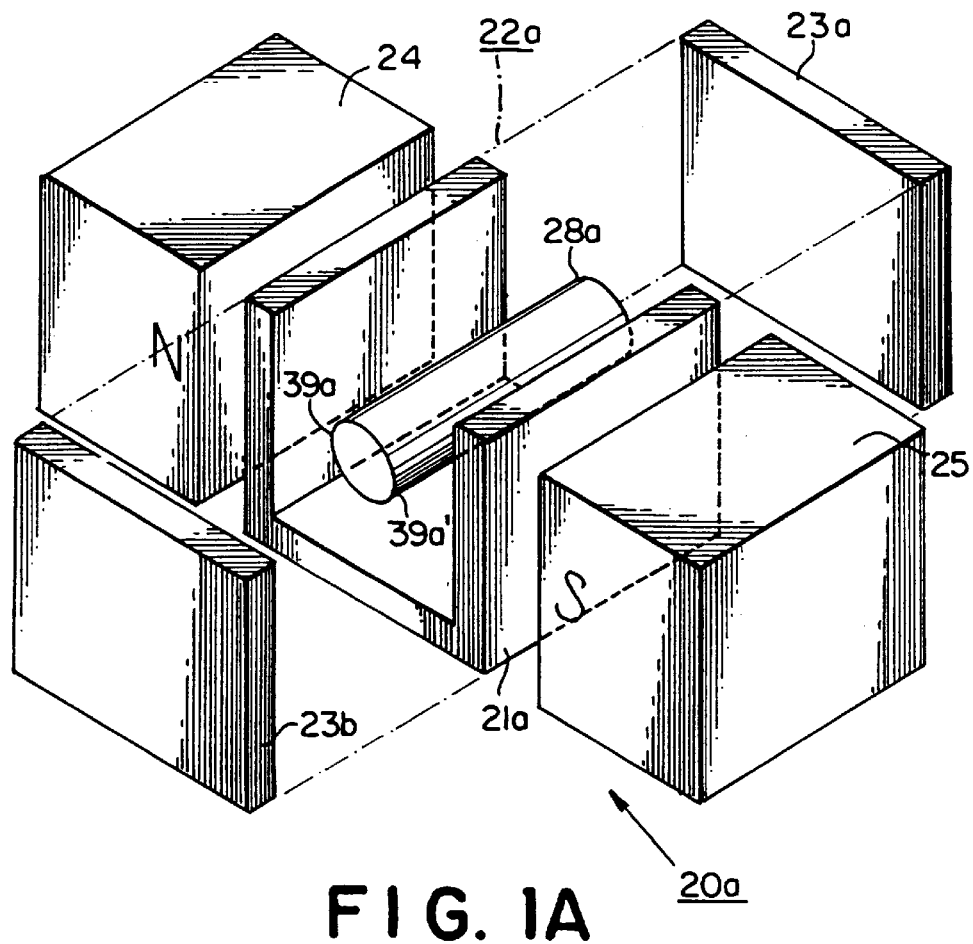

In accordance with the present invention, target entities within a fluid medium are immobilized for observation, analysis, or manipulation. Such target entities as may be immobilized hereby include cellular entities and subcellular entities.

Immobilization of a target entity is accomplished by magnetic labelling and subsequent collection of the target entity. Magnetic labelling of a target entity is achieved by the use of a colloidal suspension of magnetically-responsive particles having a coating which includes an attachment agent such as a ligand selected to bind to a corresponding receptor of the target entity. The colloidal suspension of magnetically responsive particles is mixed with the fluid medium containing the target entities to form a test medium. Such mixing can be carried out either prior to or after the fluid medium is introduced into a non-magnetic vessel. A magnetic field is then applied to the vessel.

Upon application of a magnetic field to the non-magnetic vessel, the magnetically-labelled target entities tend to migrate toward and adhere to a collection structure or magnetic flux intensifier such as a ferromagnetic wire supported within or adjacent to a vessel containing the test medium. The strength of the magnetic field, preferably between about 4 kGauss and 15 kGauss, influences the time required to effect collection. Additionally, the impact and binding forces experienced by the target entities upon the collection structure are determined in part by the strength of the applied magnetic field. The long-range attractive magnetic force acting upon the target entities within the test medium is mainly due to the size of the collection structure and the bulk permeability of the material from which the collection structure is made. The short-range binding forces between the collection structure and the collected target entities is mainly due to the surface geometry of the collection structure.

The preferred magnetic particles for use in carrying out this invention are particles that behave as true colloids. Such particles are characterized by their sub-micron particle size, which is generally less than about 200 nanometers (nm) (0.20 microns), and their stability to gravitational separation from solution for extended periods of time. Such small particles facilitate observation of the target entities via optical microscopy since the particles are significantly smaller than both the target entities and the wavelength range of visible light. Suitable magnetically-responsive particulate materials are composed of a crystalline core of superparamagnetic material surrounded by molecules which may be physically absorbed or covalently attached to the magnetic core and which confer stabilizing colloidal properties. The size of the colloidal particles is sufficiently small that they do not contain a complete magnetic domain, and their Brownian energy exceeds their magnetic moment. As a consequence, North Pole, South Pole alignment of the particles and subsequent mutual attraction/repulsion of these colloidal magnetic particles does not appear to occur even in moderately strong magnetic fields. The lack of such particle-particle interactions contributes to the stability of the colloidal suspension. Accordingly, colloidal magnetic particles are not readily separable from solution as such even with powerful electromagnets. Rather, a magnetic gradient is required within the test medium in which the particles are suspended in order to achieve separation of the discrete particles.

Magnetic particles having the above-described properties can be prepared as described in U.S. Pat. No. 4,795,698, the entire disclosure of which is incorporated by reference in the present specification, as if set forth herein in full.

For immobilization of cellular target entities, the test medium is typically prepared from appropriately prepared fluids, for example, body fluids such as blood, urine, sputum or secretions. It is preferable to add the colloidal magnetic particles to the test medium in a buffer solution. A suitable buffer solution for this purpose comprises a mixture of 5% bovine serum albumin ("BSA") and 95% of a biocompatible phosphate salt solution, optionally including relatively minor amounts of dextrose, sodium chloride and potassium chloride. The buffer solution should be isotonic, with a pH of about 7. The BSA protein serves to decrease interactions which tend to interfere with the analysis. The target substance may be added to the test medium before, after or simultaneously with introduction of the magnetic particles. The method of the invention takes advantage of the diffusion controlled solution kinetics of the colloidal magnetic particles, which may be further enhanced by the addition of heat to the test medium. The test medium is usually incubated to promote binding between the receptor and any ligand of interest present therein. Incubation is typically conducted at room temperature or at a temperature slightly above the freezing point of the test medium (i.e., 4° C. in an aqueous medium). The period of incubation is normally of short duration (i.e., about 15 minutes). The test medium may be agitated or stirred during the incubation period to facilitate contact between receptors and ligands.

Referring to FIG. 1, there is shown an exploded view of a magnetic immobilization apparatus 20a. A non-magnetic vessel, such as vessel 22a is provided with a central trough 21a and end pieces 23a and 23b for containing a fluid test medium (not shown). The vessel 22a is situated between a north pole 24 and a south pole 25 of a device for generating a magnetic field transverse to the longitudinal axis of the vessel 22a. The devices 24 and 25, shown diagrammatically in FIG. 1, may be pole pieces of an electromagnet, two confronting permanent magnets, or parts of a single channel, or a U-shaped, permanent magnet. A ferromagnetic flux intensifier, such as collection wire 28a, spans between the end pieces 23a and 23b within the vessel 22a with an orientation substantially transverse to the lines of magnetic flux between the poles 24 and 25 respectively. A ferromagnetic wire, when used as the collection structure 28a, provides localized intensification of the magnetic flux density commensurate with the curvature of the wire. The two ends of the wire 28a are attached to and are supported between the interior surfaces of the end pieces 23a and 23b so that the wire spans the interior volume of the vessel co-axially with the longitudinal axis of the wire. The two ends of the wire may be supported by, or embedded within the end pieces such that the wire is substantially straight along the entire length thereof between the end pieces. The wire 28a may have a non-magnetic coating to reduce adhesion of magnetically-responsive particles in the absence of a magnetic field.

The immobilization apparatus 20a may be mounted on a stage (not shown) having micromanipulation devices and a suitable microscope to allow an operator to manipulate and/or observe the immobilized target entities. The substantially linear form of the collection surfaces facilitates microscopic observation of the immobilized entities along the length of the collection structure since such a linear array can easily be maintained within the focal plane of a microscope. Direct observation of the immobilized entities can be made along an unobscured optical path extending into the interior of the vessel and intersecting the collection surfaces along either side of the collection structure. The vessel 22a, as shown in FIG. 1, has an open top to facilitate access to the interior by such devices as may be used in the practice of cell microsurgery or other biotechnical or chemical investigations.

Collection of target entities upon the surface of the collection wire 28a is dominant along the wire surface regions most nearly orthogonal to the lines of magnetic flux, i.e. along the opposite sides 39a and 39a' of the wire 28a which face the poles 24 and 25.

In applications wherein it is not desirable for physical contact to occur between the target entities and a metallic surface, a non-metallic coating may be applied to the surface of the ferromagnetic collection structure. When such a coating is present upon the ferromagnetic collection structure, the target entities are collected upon a collection surface that is upon the non-metallic coating and coextensive with the ferromagnetic collection structure.

When the diameter of the collector wire 28a is chosen such that the curvature of the wire 28a approximates the curvature of the target entity, linear monolayers of the target entity, or one-dimensional arrays, tend to form upon the collection wire 28a. As target entities such as cells collect upon the wire 28a, a cell which collides with another cell already attached to the wire 28a will tend to roll over the attached cell and then attach to an adjacent section of exposed wire. When a cell collides between two adjacent cells attached to the wire 28a, the two attached cells tend to move apart to accommodate attachment of the newly arrived cell to the wire. For example, it has been found that lymphocytes having a diameter on the order of 10 $\mu$m will tend to collect in linear monolayer arrays upon either side of a 0.02 mm wire from solutions wherein the number of lymphocytes is limiting. Such highly ordered collection of target entities facilitates observation as well as imaging by automatic processes.

Figures 2A, 2B:
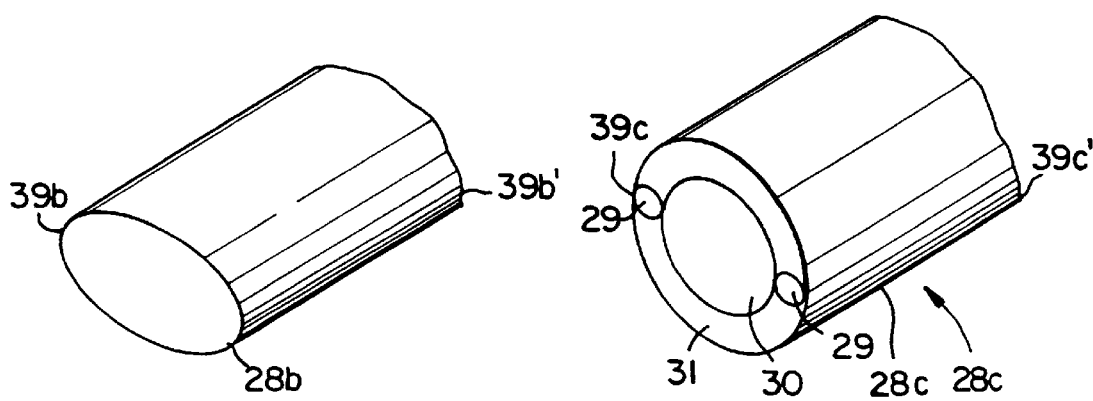
FIGS. 2A and 2B are fragmentary perspective views of ferromagnetic collecting elements suitable for use within the embodiments of FIGS. 1A–1C.

The diameter of the collection wire may be selected in accordance with the diameter of the target entities in order to produce a linear monolayer of immobilized entities. In some instances, the diameter of the target entities may be such that a corresponding cylindrical collection wire would not have enough bulk to exert a long-range influence upon the magnetic field within the vessel to attract the target entities toward the collection surface. In such instances, it may be preferable to employ a collection structure having sufficient bulk to produce a long-range magnetic gradient and also having a high curvature surface facing at least one of the magnetic pole faces. The high curvature surface serves to produce a short-range gradient in the vicinity of the collection surface to arrange the entities that have been attracted by the long-range gradient into a linear monolayer upon the collection surface. Such a collection structure may provide enhanced mechanical strength in addition to anisotropic intensification of the magnetic flux density. Such a structure is shown in FIG. 2A in the form of a wire 28b. The wire 28b has an elliptical, or ribbon-like, cross section. When the wire 28b is positioned with the major elliptical axis aligned with the magnetic flux vector of an applied magnetic field, a larger degree of flux intensification is caused along the opposite surfaces 39b and 39b' of the wire 28b having the highest curvature than along surfaces having lower curvature.

Another embodiment of a ferromagnetic collection structure for causing anisotropic flux intensification is shown in FIG. 2B. A composite wire, such as wire 28c, has a central strand 30 with two smaller strands 29 parallel to the central strand 30 and positioned along opposite sides 39c and 39c' of the central strand 30. A non-magnetic coating 31 provides support for the strand assembly and allows for ease of removal of magnetically-responsive particles in the absence of a magnetic field. When the wire 28c is placed in a magnetic field such that the lines of magnetic flux are parallel to a line defined between the centers of the smaller strands 29, maximum flux intensification is caused along the surface regions 39c and 39c' of the wire 28c which are nearest to the exterior surfaces of the smaller strands 29. Other wire geometries or configurations may be employed within the scope of the present invention in order to provide a high curvature surface while providing a greater amount of bulk material than a corresponding cylindrical wire. Such collection structures as are exemplified in FIGS. 2A–2B can be utilized within any of the several immobilization vessels described and shown herein.

Figure 3A:
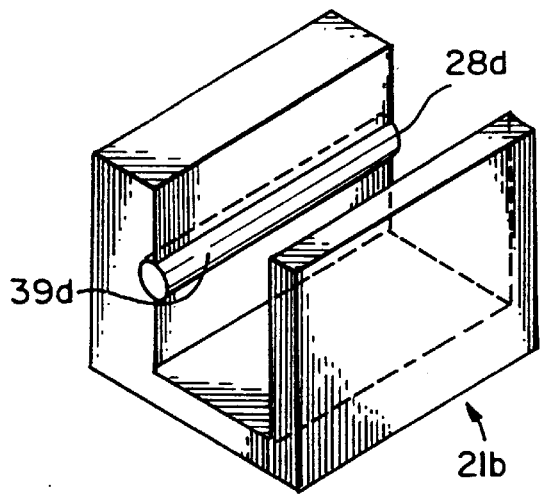
FIGS. 3A–3D are perspective views of central troughs suitable for vessels within the embodiments of FIGS. 1A–1C.
Figure 3B:
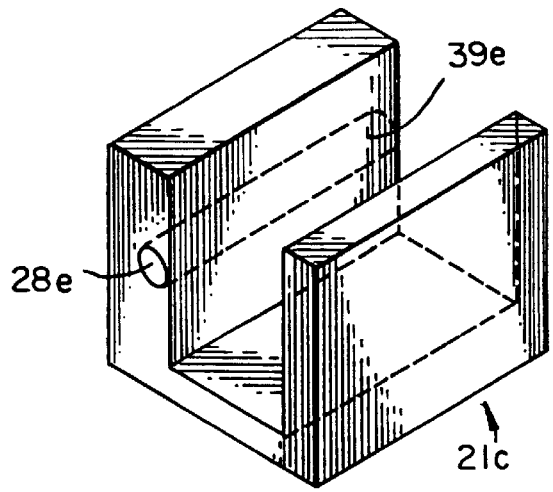

Alternative vessel structures may be used to provide enhanced spatial selectivity and mechanical support of target entity collection. In FIG. 3A there is shown a central trough 21b for such a vessel. The central trough 21b includes a ferromagnetic collection structure in the form of a wire 28d which is partially embedded in an interior lateral surface of the trough 21b. Collection of target entities in the central trough 21b will predominate along the exposed portion 39d of the surface of collection wire 28d where such entities may easily be observed. Referring to FIG. 3B, there is shown a central trough 21c having a collection structure in the form of a wire 28e embedded entirely beneath an interior lateral surface 39e of the trough 21c. Collection of target entities in a trough such as trough 21c will predominate along the interior lateral surface 39e of the trough 21c in a line parallel to the wire 28e. Such an arrangement as trough 21c provides a substantially flat collection surface and minimal visual obscuration of the target entities. Within the scope of the present invention, other geometric configurations of attached or embedded collection wires, such as rectilinear grids may be provided to produce a different pattern of target entity collection on the collection structure or on the interior surface of the trough.

Figure 3C:
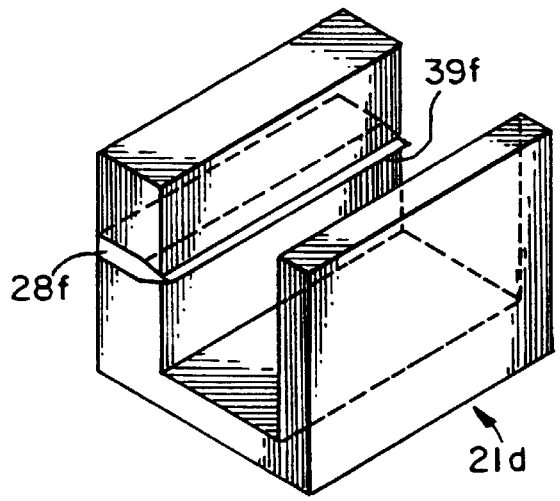

Referring now to FIG. 3C, there is shown a central trough 21d having a flat, narrow collection structure, such as a razor blade 28f, embedded within a side of the trough 21d with the edge 39f of the blade protruding into the interior of the trough and having a flat side substantially parallel to the bottom of the trough 21d. The edge 39f of collection blade 28f may have a significantly sharper or greater curvature than would be practical in embodiments employing wires suspended within a trough. Such thin wires would be fragile and unlikely to withstand magnetic field variations without substantial deformation. The angular edge 39f of collection element 28f has a high curvature which provides a high magnetic field gradient in the vicinity of the protruding edge thus promoting collection of target entities in a linear monolayer.

Figure 3D:
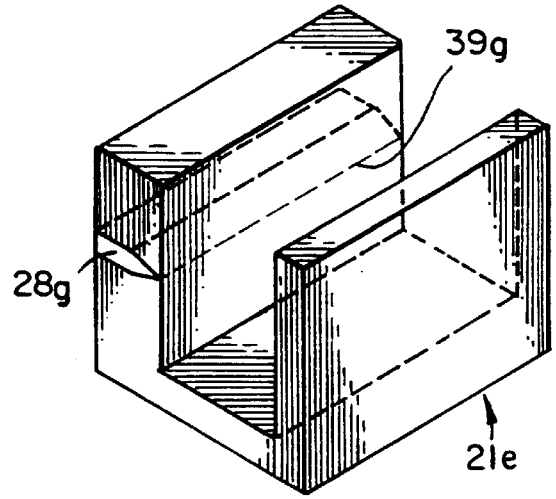

A vessel such as is shown in FIG. 3D is preferable for such applications in which a linear monolayer of target entities is desired, but where contact with the edge of the collection element would damage the target entities or be otherwise undesirable. The central trough 21e has a flat, narrow collection element 28g embedded within a side of the trough 21e in such a way that the edge of element 28g does not protrude into the interior of the trough. In this case, the target entities are collected on the interior lateral surface 39g along a line adjacent the edge of the element 28g.

Each of the trough structures described in connection with FIGS. 3A–3D may be provided with a transparent top member (not shown) or may remain open when used in an immobilization apparatus in order to provide an unobstructed observation path intersecting the collection surface or to provide direct physical access to the immobilized entities as may be desired. Additionally, the central troughs 21b–21e may be partially or entirely transparent to further facilitate such observation.

It is often desired to expose target entities to various chemical and biological environments other than the test medium in which such target entities were originally suspended. It is also often desired to rinse or flush the test medium in which the target entities have been immobilized in order to facilitate observation of the entities. Observation of the entities may be facilitated by flushing by allowing removal of an opaque medium and by allowing control of separation time so that exposure to the magnetic field may be limited to a duration sufficient for monolayer formation. A vessel which allows such environmental variation and flushing is shown in FIG. 1B. A flowthrough vessel for allowing alteration of the test environment, such as flowthrough vessel 22b, has a central trough 21f which may be of such types as troughs 21a–e discussed in connection with FIGS. 1, FIGS. 3A–3D, and FIG. 5B. Attached to the ends of the central trough 21f are end pieces 23d, 23e having one or more pairs of inlet and outlet ports such as ports 48a and 48b. The end pieces 23d, 23e also provide support for a collection wire (not shown) in embodiments employing a wire spanning between the end pieces. The ports 48a and 48b are connected with hoses 46a, 46b which may be further connected to sources of reagents, pumps, valves, and other reagent flow control devices.

The flowthrough vessel 22b is provided with a top 40, which may be transparent to provide a clear optical path for microscopic observations. For such observations wherein visible light or other electromagnetic radiation is observed after transmission through the subject of interest, the bottom 41 of the central trough 21f may also be transparent to allow the passage of light through the vessel. In alternative embodiments, the top 40 or any other parts of the vessel may be selectively transparent to portions of the electromagnetic spectrum as may be desired in photobiological investigations. In still other embodiments, the top 40 and the bottom 41 of the central trough 21f may form a polarizer/analyzer pair for such applications as optical studies of the mechanical properties of transparent membranes.

The flowthrough vessel 22b allows sequential exposure to reagents, such as is required by indirect fluorescent MAb labelling, while significantly reducing the loss of target entities as is usual in traditional methods which necessitate multiple washings and centrifugations. The flowthrough vessel 22b further allows for the consumption of a reduced volume of reagents in such sequential processes since target entities are collected in a relatively high concentration and with reduced spatial extent relative to known separation devices. The hoses 46a, 46b may be connected to a reagent recirculation system for further economy of reagent consumption.

Figure 1C:
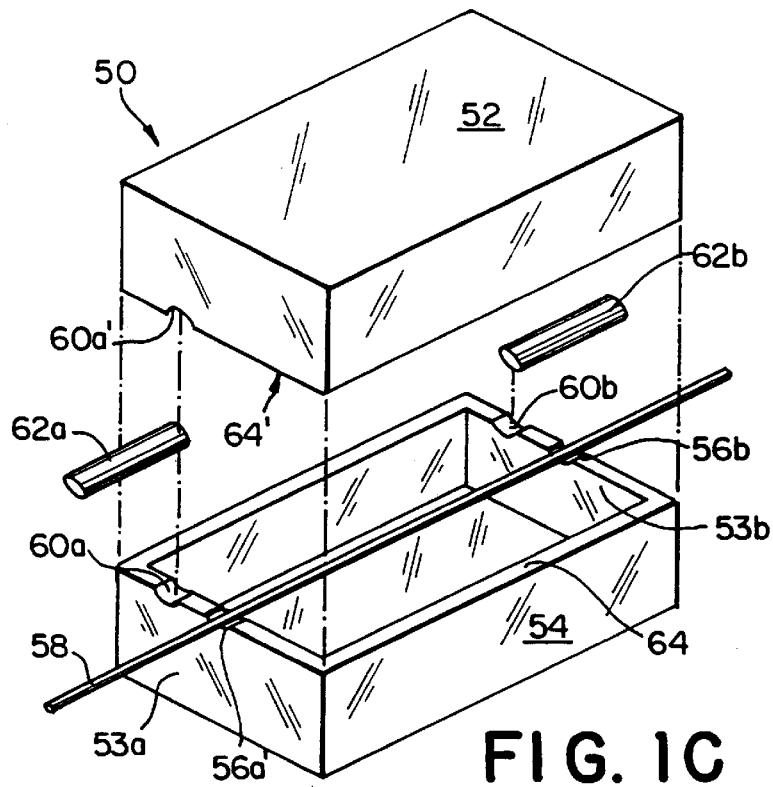

A preferred manner of constructing an immobilization vessel is illustrated in FIG. 1C. The vessel 50 includes an upper assembly 52 and a lower assembly 54 which mate along surfaces 64 and 64' to form a substantially rectangular hollow enclosure. The upper assembly 52 and the lower assembly 54 are both transparent and have substantially flat exterior surfaces so that light may pass through the vessel 50 along a substantially unobstructed and non-distorting optical path. Opposed ends 53a and 53b of the lower assembly 54 have notches or grooves 56a and 56b formed along respective upper edges of the ends 53a and 53b. Before the upper assembly is secured to the lower assembly, a ferromagnetic collection structure 58 may be aligned within grooves 56a and 56b and secured therein by an adhesive (not shown). Additional adhesive is applied to the mating surfaces 64 and 64' of the upper and lower assemblies and the mating surfaces are brought into contact with each other. After the adhesive has set, the protruding portions of the collection structure 58 may be trimmed flush with the exterior of the vessel.

In order to provide a flowthrough vessel, semicircular notches 60a, 60a', and 60b may be formed the opposed ends of the upper and lower assemblies along the mating surfaces 64, 64'. When the upper and lower assemblies are secured together, inlet port nipple 62a and outlet port nipple 62b may be positioned so that the nipples 62a and 62b are secured within the mated semicircular notches. The flow path is through the hollow inlet nipple 62a, the hollow interior of the enclosure formed by the assemblies 52 and 54, and the hollow outlet nipple 62b. Other methods of assembling an immobilization apparatus, such as injection molding, are contemplated within the scope of the invention.

Figure 5:
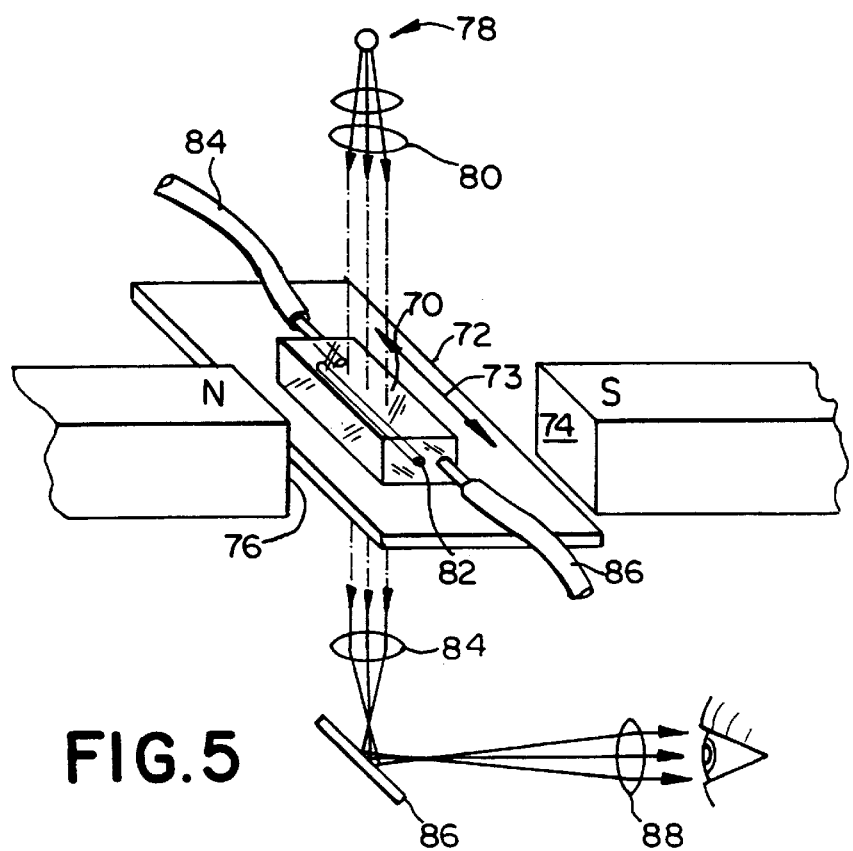
FIG. 5 is a schematic diagram of an arrangement for observing and manipulating entities collected within a magnetic immobilization apparatus.

Turning now to FIG. 5, there is shown an exemplary arrangement in which observations of immobilized target entities can be made. A hollow vessel 70, which may be of any type discussed herein, is supported upon a microscope stage 72. The microscope stage 72 is equipped with a well-known mechanism for translating the vessel 70 in either direction along the axis 73. Magnets 74 and 76 are positioned on either side of the microscope stage to establish an applied magnetic field transverse to the longitudinal axis of the vessel 70. A source of light 78 is provided for projecting a collimated beam 80 of light toward the vessel 70 along an axis that is perpendicular to the longitudinal axis of the vessel and to the applied magnetic field. The vessel 70 has a top and a bottom that are transparent to the beam 80 of light. The top and bottom surfaces of the vessel 70 are substantially flat so that the beam 80 may pass through the top and bottom surfaces substantially undistorted. A ferromagnetic collection structure 82 is positioned within the vessel 70 and in the present instance is supported co-axially of the longitudinal axis of the vessel 70. The ferromagnetic collection structure 82 has a coextensive collection surface upon which magnetically-labeled entities are adhered. The collection surface of the collection structure 82 is oriented relative to the path of beam 80 such that the optical path of the beam 80 intersects the collection surface so that the immobilized entities may be visually observed. Such visual observation may be made, for example, by collecting the light transmitted through the vessel 70 with an objective lens 84 and reflecting the collected light with a mirror 86 toward an eyepiece 88.

Lateral translation of target entities along the collection surface may be accomplished within an immobilization apparatus without necessitating physical contact between the target entities and a device such as a micromanipulator. A magnetic field generated between two confronting poles of finite lateral extent possesses a positive lateral gradient toward the region between the poles. Hence, magnetically-labeled target entities which have been collected on a ferromagnetic collecting structure such as the wire 28a shown in FIG. 1A will tend to remain between the poles 24 and 25 as the vessel 22a is translated in a direction parallel to the longitudinal axis of the wire 28a. The relative motion between a ferromagnetic collecting element and a target entity generated in such a fashion may be used to position a target entity at a selected location upon the surface of the ferromagnetic collecting element.

Lateral translation of target entities along the collection surface may also be employed to increase the local concentration of target entities which have been collected. Referring to FIG. 4A, an alternative collection structure is shown as a collection wire 28h having a reduced diameter at 34 and an enlarged diameter at 35 interconnected by a transverse wall 36 to produce a shoulder therebetween. The collection wire 28h is positioned between confronting opposite magnetic poles 24 and 25 within a vessel (not shown) containing a fluid medium in which are suspended magnetically-labeled target entities. The confinement of magnetic flux lines between poles 24 and 25 will cause collection of target entities along the portion of the outer sides of the wire 28h in the reduced diameter portion 34 which is disposed directly between the poles 24 and 25. The vessel supporting the wire 28h is then laterally translated, such as by translation of a supporting microscope stage (not shown), in the direction indicated by the arrow 38h so as to move the enlarged portion 35 of the wire 28h into the region between the poles 24 and 25. The tendency of magnetically-responsive target entities to remain in the region of greatest magnetic flux density will cause the target entities to congregate on the portions of the collection surfaces 39h and 39h' adjacent the opposite shoulders 37 and 37' between the anterior wall surface 36 of the enlarged portion 35 and the opposite sides 39h, 39h' of the reduced-diameter wire portion 34 facing the poles 24 and 25.

Lateral translation and congregation of the target entities may also be accomplished using vessels having embedded ferromagnetic collection structures similar to those shown in central troughs 21b–21e shown in FIGS. 3A–3D. Referring to FIG. 4B, a central trough 21i having an embedded ferromagnetic collection element 28i is shown. The central trough 21i further includes a surface irregularity, such as a transverse obstacle or weir 48, forming a shoulder on the interior surface 39i located along the line of collection. As the central trough 21i is laterally translated in the direction indicated by the arrow 38i, target entities collected upon the interior surface 39i of the central trough will tend to congregate at the angular junction between the line of collection and the anterior surface 49 of the shoulder 48. The ability to create dense congregations of target entities without direct mechanical interventions provides unique advantages for such applications as in vitro fertilization or other techniques in which it is desired to propagate a culture of fragile target entities which reproduce at a rate commensurate with their concentration.

The following examples further describe in some detail manners of using aspects of the present invention and set forth the best mode contemplated by the inventors for carrying out the invention, but are not to be construed as limiting the invention.

EXAMPLE 1

To demonstrate the feasibility of one-dimensional immobilization of cells within a test medium, an immobilization apparatus using a central trough of the type shown in FIG. 3C was constructed and tested. Permanent rare earth alloy magnets made of CRUMAX 355 (a trademark of Crucible Magnetics of Elizabethtown, Ky.) were used to generate the magnetic field. The magnets were in the form of bar magnets having dimensions of 1.75 inches×0.375 inches×0.375 inches with a flux vector parallel to one of the 0.375 dimensions. The magnets were mounted in a yoke made of cold rolled steel. The opposing faces of the magnets were 0.3125 inches apart. The magnetic field strength at each bar magnet face was measured to be 5.8 kGauss. The vessel had outer dimensions of 0.1875 inches×0.3125 inches×0.5 inches with the 0.3125 inch dimension fitted between the magnet faces. The wall thickness of the vessel was 0.0625 in. The ferromagnetic collection element was a portion of a razor blade.

A dextran-coated magnetic colloid was prepared having a concentration of 0.0212 $\mu$g/ml of Fe. Five ml of the magnetic colloid was incubated with cells of the T-Cell CEM line. The colloid coated the cells via non-specific binding. The final concentration of T-Cells in the mixture was 2,000 cells/ml. Next, 50 $\mu$l aliquots of the cell mixture were inserted into the immobilization vessel and allowed to separate for 5 minutes. Excess cells were flushed away with PBS buffer. A single line of cells collected along the edge of the razor blade were observed with an optical microscope at 30×magnification.

EXAMPLE 2

To demonstrate chemical manipulation of cells subsequent to immobilization, T-Cells were first immobilized as in Example 1 above. After collection, the cells were washed three times in the usual manner with PBS buffer to remove excess magnetic particles from the mixture. Then, 12 $\mu$l of Fitc CD45 T-Cell marker having a concentration of 10 $\mu$g/ml was added to the cell mixture and incubated for five minutes at room temperature. After the labelling step, the cells were washed three times again in PBS buffer. Fluorescently-labelled cells were observed to be aligned with the edge of the razor blade via 60×magnification fluorescent microscopy.

EXAMPLE 3

To demonstrate micromanipulation of cells subsequent to immobilization, 2,000 magnetically labeled T-Cells in 20 $\mu$l of 10 mM PBS buffer were injected into the immobilization vessel and separated as in Example 1. The cells were subsequently washed with PBS buffer to remove any unbound cells or cellular debris. Acridine Orange was allowed to flow past the immobilized cells. Using an optical microscope at 600×magnification, the cell nuclei appeared to glow a bright orange. 1591 immobilized cells were counted optically. The cells were then allowed to incubate for a period of 5 hours. A secondary stain, DIL-282, available from Molecular Probes of Eugene, Oreg., was injected in to the chamber to selectively stain the portions of the cell surfaces not in direct contact with the razor edge or neighboring cells. The cells were then washed twice in PBS buffer. The immobilization vessel was taken out of the magnetic field to effect re-orientation of the cells and agitated for one minute. The vessel was then placed back into the magnetic field. Surface portions of cells which had previously been in direct contact with neighboring cells surfaces were visible and unstained. Sections of such unstained cell membranes were surgically removed for a comparison of the chemical composition of such sections with comparable sections of stained cell membrane in order to identify chemical cellular communication agents.

From the foregoing disclosure and the accompanying drawings, it can be seen that the present invention provides certain novel and useful features that will be apparent to those skilled in the pertinent art. In particular there has been described an apparatus in which biological entities are biospecifically magnetically labeled and immobilized. Such an apparatus provides rapid immobilization of target entities while they may remain within a fluid medium thus retaining viability and avoiding potentially damaging physical contact as occurs in techniques available hitherto. The apparatus disclosed herein further facilitates observation and manipulation of the immobilized entities by manual and automated techniques. Various embodiments of the present invention allow arbitrary configurational capture, spatial translation, and sequential reagent exposure of the target entities.

The terms and expressions which have been employed are used as terms of description and not of limitation and there is no intention in the use of such terms and expressions of excluding any equivalents of the features shown and described, or portions thereof, but it is recognized that various modifications are possible within the scope of the invention claimed.

We claim:

1. An apparatus for immobilized magnetically-labeled cells suspended in a fluid medium, the apparatus comprising:

magnetic means for producing a magnetic field;

a nonmagnetic vessel defining a chamber for containing the fluid medium within said magnetic field, said vessel having a longitudinal axis and two opposed ends intersecting said longitudinal axis, wherein said longitudinal axis is aligned perpendicularly to flux lines of said magnetic field;

a ferromagnetic collection structure supported within the chamber for causing a localized intensification of the magnetic field within the vessel whereby the magnetically-labeled cells are attracted toward said structure, said ferromagnetic collection structure comprising a substantially linear elongated member aligned in parallel with said longitudinal axis and spanning between said opposed ends, said vessel including means for defining an observation path along a lateral axis orthogonal to said longitudinal axis for allowing substantially unobstructed microscopic observation of cells attracted to said collection structure; and a collection surface coextensive with the elongated member of said ferromagnetic collection structure and intersecting said observation path for immobilizing the cells for said microscopic observation along said path, said collection surface sized relative to the cells for causing a sufficiently high localized intensification of the magnetic field for producing a substantially one-dimensional monolayered spatial distribution of the cells adjacent thereto; and wherein the collection structure is spaced apart from all interior surfaces of the chamber that extend generally parallel to said longitudinal axis with sufficient clearance to permit access of cells to the entire exterior surface of said collection structure disposed within the chamber for monolayered collection adjacent to the collection surface.

2. An apparatus as recited in claim 1 wherein said means for defining an observation path for allowing microscopic observation includes a transparent member that is transparent to at least a selected portion of the electromagnetic spectrum.

3. An apparatus as recited in claim 1 wherein said means for defining an observation path for allowing microscopic observation comprises an aperture in said vessel for allowing physical access to the cells.

4. An apparatus as recited in claim 1 wherein the collection surface is sized to immobilize a linear monolayer of cells having a diameter of approximately 10 $\mu$m.

5. An apparatus for immobilizing magnetically-labeled entities suspended in a fluid medium, the apparatus comprising:

magnetic means for producing a magnetic field;

a nonmagnetic vessel defining a chamber for containing the fluid medium within said magnetic field, said vessel having a longitudinal axis and two opposed ends spaced along said longitudinal axis, wherein said longitudinal axis is aligned perpendicularly to flux lines of said magnetic field;

a ferromagnetic collection structure supported within the chamber for causing a localized intensification of the magnetic field within the vessel whereby the magnetically-labeled entities are attracted toward said structure, said ferromagnetic collection structure comprising a substantially linear elongated member aligned in parallel with said longitudinal axis and spanning between said opposed ends, said vessel having an aperture for defining an observation path perpendicular to the longitudinal axis for allowing substantially unobstructed microscopic observation of entities attracted to said collection structure, and for allowing lateral physical access to the entities; and a collection surface coextensive with the elongated member of said ferromagnetic collection structure, intersecting said observation path, and immobilizing the entities for said microscopic observation and physical access along said path.

6. An apparatus as recited in claim 5 for immobilizing entities having a known diameter wherein said collection structure sized to approximate the known diameter and for causing sufficiently high localized intensification of the magnetic field for producing a substantially monolayered one-dimensional spatial distribution of the entities thereon.

7. An apparatus as recited in claim 5 wherein the collection surface is configured to immobilize entities having a diameter of approximately 1 $\mu$m.

8. An apparatus for immobilizing magnetically labeled entities suspended in a fluid medium, the apparatus comprising:

magnetic means for producing a magnetic field;

a non-magnetic vessel having a base configured for support upon a translatable stage for translating the vessel within the magnetic field, the vessel defining a chamber bounded by interior surfaces of the vessel for containing the fluid medium within said magnetic field, said vessel having a longitudinal axis and lateral axes defining a chamber having a width and a height, and two opposed ends intersecting the longitudinal axis to define a chamber length, and said vessel having means for defining a lateral observation path including a transparent member that is transparent to at least a selected portion of the electromagnetic spectrum for allowing microscopic observation of the immobilized entities;

a ferromagnetic collection structure supported in the vessel in parallel with the longitudinal axis for causing a localized intensification of the magnetic field within the chamber whereby the magnetically-labeled entities are attracted toward said structure, said ferromagnetic collection structure comprising a substantially linear elongated member spanning between said opposed ends and having an effective diameter substantially less than the chamber height and width; and a longitudinal collection surface coextensive with said ferromagnetic collection structure and intersecting said observation path to immobilize the entities for said microscopic observation along said path.

9. An apparatus for immobilizing magnetically-labeled microscopic biological specimens in a fluid medium for microscopic observation, comprising:

a non-magnetic vessel movably supportable relative to a microscope, the vessel having a pair of lateral axes that are orthogonal to one another and a longitudinal axis that is orthogonal to said lateral axes, a chamber for containing the fluid medium and having a substantially flat transparent surface providing an observation path into the chamber along one of said lateral axes;

a ferromagnetic collection structure comprising a linear elongated member positioned in parallel with the longitudinal axis of the chamber for causing a localized intensification of an applied magnetic field within the vessel whereby the magnetically-labeled specimens are attracted toward the structure; and a collection surface coextensive within the elongated member of the collection structure and having a diameter less than both lateral dimensions of the chamber measured along said lateral axis to immobilize a linear monolayer of magnetically-labeled specimens thereon, and intersecting the observation path to hold said linear monolayer within the focal plane of the microscope.

10. The apparatus of claim 9 wherein said diameter is sized to immobilize biological specimens having a diameter on the order of 10 μm.

11. The apparatus of claim 9 wherein the collection structure is supported by and along a longitudinal wall of the vessel.

* * * * *